US007758869B2

(12) United States Patent
Aldwell et al.

(10) Patent No.: US 7,758,869 B2
(45) Date of Patent: Jul. 20, 2010

(54) IMMUNOGENIC COMPOSITIONS

(75) Inventors: Frank Ernest Aldwell, Dunedin (NZ); Bryce Malcolm Buddle, Upper Hutt (NZ); Ian George Tucker, Dunedin (NZ)

(73) Assignee: Immune Solutions Limited, Dunedin (NZ)

( * ) Notice: Subject to any disclaimer, the term of this patent is extended or adjusted under 35 U.S.C. 154(b) by 387 days.

(21) Appl. No.: 10/484,688

(22) PCT Filed: Jul. 26, 2002

(86) PCT No.: PCT/NZ02/00132

§ 371 (c)(1), (2), (4) Date: Jun. 30, 2004

(87) PCT Pub. No.: WO03/009868

PCT Pub. Date: Feb. 6, 2003

(65) Prior Publication Data

US 2004/0234533 A1 Nov. 25, 2004

(30) Foreign Application Priority Data

Jul. 26, 2001 (NZ) .................................... 513169

(51) Int. Cl.
*A61K 39/02* (2006.01)
*A61K 39/04* (2006.01)
*A61K 49/00* (2006.01)

(52) U.S. Cl. ...................... 424/234.1; 424/9.1; 424/9.2; 424/184.1; 424/204.1; 424/248.1; 424/278.1

(58) Field of Classification Search .................. 424/9.1, 424/9.2, 184.1, 204.1, 234.1, 248.1, 278.1, 424/1.21, 1.29, 9.32, 812; 264/4, 4.1
See application file for complete search history.

(56) References Cited

U.S. PATENT DOCUMENTS

| | | | | |
|---|---|---|---|---|
| 5,650,152 A | | 7/1997 | Anderson et al. | 424/195 |
| 5,683,722 A | | 11/1997 | Derrieu et al. | |
| 5,716,637 A | * | 2/1998 | Anselem et al. | 424/450 |
| 5,849,307 A | | 12/1998 | Metz et al. | 424/278 |
| 6,146,632 A | | 11/2000 | Momin et al. | 424/184 |

FOREIGN PATENT DOCUMENTS

| | | |
|---|---|---|
| EP | 0 544 612 A2 | 6/1993 |
| NZ | 211667 | 12/1989 |
| WO | WO93/16728 | 9/1993 |
| WO | WO94/16681 | 8/1994 |
| WO | WO 00/41682 | 7/2000 |
| WO | WO 01/75096 | 10/2001 |

OTHER PUBLICATIONS

Gregoriadis, G., "Liposomes as immunological adjuvants for protein and peptide vaccines", Drug Targeting and Delivery, vol. 6, pp. 1-18, 1995.*

Gursel, I., et al. "Giant liposomes as potential vesicles for live or attenuated microbial vaccines", Drug Targeting and Delivery, vol. 6, pp. 35-50, 1995.*

Saxegaard, The Veterinary Record 116, 1985, pp. 439-441, Control of paratuberculosis (Johne's disease) in goats by . . . .

Gheorghiu et al, New Approaches to Stabilisation . . . vol. 87, 1996, pp. 251-261, Stabilisation of BCG Vaccines.

Doherty et al, Infection & Immunity, Jun. 2002, pp. 3111-3121, Oral Vaccination with Subunit Vaccines Protects Animals . . . .

D'Souza et al, Infection & Immunity, Jul. 2002, pp. 3681-3688, Improved Tuberculosis DNA Vaccines by Formulation in Cationic . . . .

Manabe et al, Infection & Immunity, Mar. 2002, pp. 1566-1570, Naturally Attenuated, Orally Administered Mycobacterium . . . .

Griffin et al., Tubercle and Lung Disease, vol. 79, No. 3, 1999, pp. 135-143, Vaccine protocols to optimise the protective efficacy of BCG.

Griffin et al. Immunology & Cell Biology, vol. 71, 1993, pp. 559-570, BCG vaccination in deer: Distinctions between delayed type hypersensitivity and laboratory parameters of immunity.

Saxegaard, The Veterinary Record 116, 1985, pp. 439-441, Control of paratuberculosis (Johne's disease) in goats by vaccination.

Aldwell et al., New Zealand Veterinary Journal, vol. 43, No. 7, 1995, pp. 356-359, Route of BCG administration in possums affects protection against bovine tuberculosis.

Aldwell et al., Immunology & Cell Biology, vol. 74, 1996, pp. 45-51, Bacterial metabolism, cytokine mRNA transcription and viability of bovine alveolar macrophages infected with *Mycobacterium bovis* BCG or virulent *M. bovis*.

Aldwell et al., Immunology & Cell Biology vol. 75, 1997, pp. 161-166, Sequential activation of alveolar macrophages by IFN-γ and LPS is required for enhacned growth inhibition o f virulent . . . .

Buddle et al., Int J Tuberc Lung Dis vol. 1, No. 4, 1997, pp. 377-383, Intraduodenal vaccination of brushtail possums with bacille Calmette-Guerin enhances immune responses and protection . . . .

Buddle et al., Veterinary Microbiology, vol. 38, 1994, pp. 241-254, Experimental *Mycobacterium bovis* infection in the brushtail possum (*Trichosurus vulpecula*): pathology, . . . .

Daugelat et al., Infection & Immunity, Vol. 63, No. 5, May 1995, pp. 2033-2040, Influence of Mouse Strain and Vaccine Viability on T-Cell Responses Induced by *Mycobacterium bovis* . . . .

Gheorghiu et al., New Approaches to Stablisation of Vaccines Potency. vol. 87, 1996, pp. 251-261, Stablisation of BCG Vaccines.

Lagranderie et al., Vaccine, vol. 18, 2000, pp. 1186-1195, Immunogenicity and protective capacity of *Mycobacterium bovis* BCG after oral or intragastric administration in mice.

Masarova et al., Biotechnol Appl Biochem, vol. 34, 2001, pp. 127-133, Stability enhancement of *Escherichia coli* penicillin G acylase by glycosylation with yeast mannan.

(Continued)

*Primary Examiner*—Rodney P. Swartz
(74) *Attorney, Agent, or Firm*—D. Benjamin Borson

(57) ABSTRACT

The invention relates to immunogenic compositions and to methods for immunizing animals using the same. The immunogenic composition comprises a lipid formulation most usually in solid form, and at least one immunogenic component. A preferred immunogenic component is a living organism. In a preferred embodiment the composition is formulated for oral administration.

54 Claims, 7 Drawing Sheets

OTHER PUBLICATIONS

Mossiron et al., LIPIDS, vol. 14, No. 4, 1979, pp. 391-394, Influence of Elevated Levels of Linoleic Acid on the Thermal Properties of Bovine Milk Fat.

Doherty et al., Infection & Immunity, vol. 70, No. 6, Jun. 2002, pp. 3111-3121, Oral Vaccination with Subunit Vaccines Protects Animals against Aerosol Infection with *Mycobacterium tuberculosis*.

D'Souza et al., Infection & Immunity, Vo. 70, No. 7, Jul. 2002, pp. 3681-3688, Improved Tuberculosis DNA Vaccines by Formulation in Cathionic Lipids.

Manabe et al., Infection & Immunity, vol. 70, No. 3, Mar. 2002, pp. 1566-1570, Naturally Attenuated, Orally Administered *Mycobacterium microti* as a Tuberculosis Vaccine Is Better than Subcutaneous *Mycobaterium bovis* BCG.

European Search Report dated Jun. 4, 2008.

* cited by examiner

IMMUNOGENIC COMPOSITIONS

This is a nationalization of PCT/NZ02/00132 filed Jul. 26, 2002 and published in English. Foreign priority based on New Zealand application No. 513169, filed Jul. 26, 2001, is claimed under 35. U.S.C. §119.

TECHNICAL FIELD

The present invention broadly relates to the use of lipids to formulate immunogenic compositions, particularly live bacterial vaccines, and to methods for immunizing animals using the compositions.

BACKGROUND

Most human and animal pathogens including those that cause tuberculosis (TB), initiate infection via the mucosal surfaces. Accordingly, protective immunity against such pathogens may require induction of strong mucosal immune responses. However, mucosal immune responses are generally weak following parenteral immunization. Despite the obvious need for vaccines, particularly TB vaccines, to protect against mucosal sites, the vaccines in use today are given by intradermal or subcutaneous injection. The development of more effective compositions, and/or delivery systems for vaccines by alternate routes is therefore desirable. Oral administration of vaccines in particular has a number of advantages including ease of administration and targeting of the mucosal immune response. Despite this, oral vaccination of animals and man to provide mucosal and/or systemic immunity has to date been largely ineffective. Efficacy of such vaccines has been hampered by degradation of the vaccine as it passes through the gut. In particular, most antigenic compounds possess peptide bonds that are readily broken down by gastric and proteolytic enzymes in the gut.

A number of vaccines rely on the use of freeze-dried preparations of organisms. For example, the current vaccine for human TB is based on freeze-dried preparations of a live attenuated bacterium called Bacille Calmette Guerin (BCG). However, it has been shown that freeze-drying procedures result in 30 to 50% loss of viability of BCG and impaired recovery of remaining live bacteria (7). A composition which retains greater viability of organisms prior to use would contribute greatly to the effectiveness of such vaccines.

To improve immune responses, antigens have been mixed with a number of adjuvant substances to stimulate immunogenicity. These adjuvants are primarily alum and oil-in-water emulsions. The latter group is typified by the Freund's mineral oil adjuvants. However, the use of Freund's complete adjuvant (FCA) in human and veterinary vaccines is contraindicated because of toxic reactions that have been reported. For these reasons, Freund's adjuvant may also be unsuitable for oral administration.

In other oil-in-water emulsions surfactants have been required because of the high oil content. Detergent properties of surfactants render them unsuitable for parenteral or oral administration. Further, toxic reactions even for approved surfactants have been reported. A further drawback with emulsions are that they are heterogeneous systems of one immiscible liquid dispersed in another. This is unstable and results in separation of the aqueous phase over time. This poses difficulties for maintaining vaccines in stable suspension. Moreover, antigens trapped in the aqueous phase of water-in-oil emulsions are unlikely to be protected from degradation in the stomach.

Liposomes and lipid vesicles have also been explored for use with vaccines, particularly with small antigenic components that may be readily encapsulated. Generally, liposomes and vesicles are not useful for encapsulation of large antigens such as live microorganisms. Moreover, liposomes and vesicles are costly and time consuming to produce, and the extraction procedures used in their preparation may result in alteration of the chemical structure or viability of vaccine preparations and hence their immunogenicity. For example, heat and solvents may alter the biological integrity of antigenic components such as proteins.

It is therefore an object of the present invention to provide an immunogenic composition and/or delivery system which addresses these desiderata or which at least provides the public with a useful choice.

SUMMARY OF THE INVENTION

Accordingly, in a first aspect the present invention provides an immunogenic composition comprising a pharmaceutically acceptable lipid formulation and at least one immunogenic component comprising an immunogenically effective amount of live organisms, the composition being formulated for oral administration.

Preferably, the lipid formulation is in solid or paste form.

In a further aspect the present invention provides an immunogenic composition comprising a pharmaceutically acceptable lipid formulation which is in solid form and undergoes solid to fluid transition between about 10° C. to 40° C., and at least one immunogenic component present in an antigenically effective amount.

Preferably, the lipid formulation undergoes solid to fluid transition between about 30° C. to 40° C.

Preferred lipid formulations for use in the compositions of the invention contain long chain fatty acids.

In terms of fatty acid composition, a preferred lipid formulation contains 40% to 100%, preferably 60% to 100%, more preferably 80% to 100%, and even more preferably 90% to 100% $C_{16}$ and/or $C_{18}$ fatty acids.

A further preferred composition has a lipid formulation which contains less than 35%, preferably less than 25%, and more preferably less than 10% $C_{14}$ fatty acids or shorter.

In one embodiment, the lipid formulation contains:

20% to 60% saturated fatty acids;

25% to 60% monounsaturated fatty acids; and 0.5 to 15% polyunsaturated fatty acids.

In a particularly preferred composition, the lipid formulation contains:

35% to 50% saturated fatty acids;

40% to 55% monounsaturated fatty acids; and

5% to 9% polyunsaturated fatty acids.

The current preferred lipid formulation for use in the invention has the formula: 3% myristic acid; 26% palmitic acid; 15% stearic acid; 40% oleic acid; and 6% linoleic acid.

The immunogenic component may be a protein, glycoprotein, peptide or factor with a protein or peptide component.

In one embodiment, the immunogenic component comprises live organisms. Preferably, as a biologically pure culture.

Preferably, the live organisms in the compositions of the invention are bacteria, particularly non-pathogenic bacteria, and more preferably bacteria belonging to the genus *Mycobacterium*. A particularly preferred mycobacterium for use in the invention is *Mycobacterium bovis* BCG.

In one embodiment, the composition comprises at least two immunogenic components. The first is preferably a live organism and the second immunogenic component is preferably derived from an infectious agent, or is a weakly immunogenic protein or peptide.

In a further aspect, the invention provides a method for preparing an immunogenic composition of the invention, the method comprising mixing the immunogenic component(s) with the lipid formulation.

In a still further aspect, the invention also provides a method for immunizing an animal, the method comprising administering to said animal an immunogenic composition of the invention.

In a further aspect, the invention provides a method for stimulating a mucosal immune response in an animal, the method comprising administering to said animal an immunogenic composition of the invention.

Administration of the composition in these methods is preferably by the oral route The invention also relates to the use of lipid formulations in the preparation of the immunogenic compositions of the invention.

BRIEF DESCRIPTION OF THE DRAWINGS

Aspects of the invention will now be described in relation to the accompanying drawings in which.

DETAILED DESCRIPTION

Figure 1:
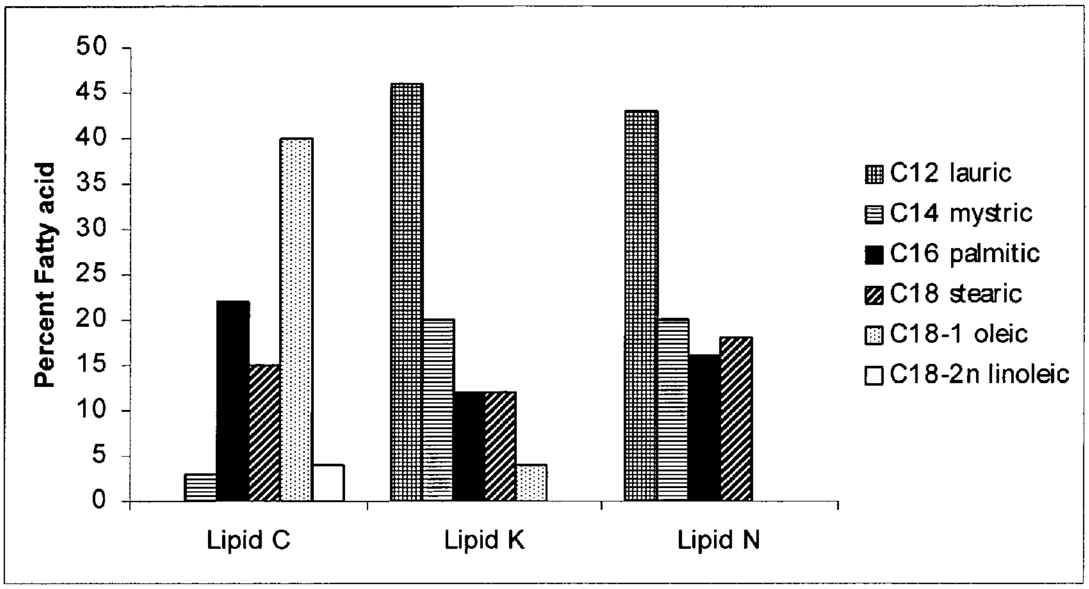
FIG. 1. Fatty acid composition of lipid formulations. Lipids were analysed by gas chromatography according to standard protocols. The fatty acid composition of each lipid is expressed as a percentage of the total fatty acid composition.

Accordingly, in a first aspect, the invention provides an immunogenic composition comprising a pharmaceutically acceptable lipid formulation and at least one immunogenic component comprising an immunogenically effective amount of live organisms, the composition being formulated for oral administration.

Preferably, the lipid is in solid form. Conveniently, the lipid is in solid form at 10° C. or above.

In a further aspect the present invention provides an immunogenic composition comprising a pharmaceutically acceptable lipid formulation which is in solid form and undergoes solid to fluid transition between about 30° C. to 40° C., and at least one immunogenic component present in an immunogenically effective amount.

The lipids employed in the formulations above are preferably suitable for animal or human administration including consumption and may be selected from a broad range of natural (vegetable or animal derived), or synthetic lipid products including oils, fats and waxes.

Most usually, the lipid material will be liquid at temperatures above about 30° C. That is, the lipid should be selected to achieve melting point at physiological temperature in the animal to which it is administered, most usually by the oral route. Desirably, the lipid will be in the form of a solid at 10-30° C. at atmospheric pressure, and preferably is still solid at from 20° C. to 30° C. at atmospheric pressure. However the melting temperature of lipid is not exclusive and may include oils, fats and waxes with a range of melting temperatures.

Preferred lipids for use herein will undergo transition from the solid phase to the liquid phase between about 30° C. and physiological temperature of about 40° C., commonly 37° C. Summaries of lipid phase behaviour are available in the art, see for example (10). Accordingly, a skilled reader can select a lipid having the desired properties and melt point based on information in the art and simple experiment.

Suitable lipid formulations are triglycerides including glyceryl esters of carboxylic acids, compounds consisting of an aliphatic chain and a —COOH end, and saturated and non-saturated fatty acids and mixtures thereof.

Currently preferred lipids are triglycerides containing primarily $C_8$ to $C_{20}$ acyl groups, for example myristic, palmitic, stearic, oleic, linoleic, parinic, lauric, linolenic, arachidonic, and eicosapentaenoic acids, or mixtures thereof.

It has also been determined that for lipid formulations useful in the invention longer chain fatty acids, for example, $C_{16}$-$C_{18}$, are preferred. Long chain fatty acids have been found to be more effective in protecting organisms such as BCG in vaccines given to mice and possums. Viewed in this way, lipid formulations preferred for use in the invention contain: 40% to 100%, preferably 60% to 100%, preferably 80% to 100%, and more preferably 90% to 100% C.sub.16 and/or C.sub.18 fatty acids.

Generally, $C_{16}$ fatty acids represent from 10% to 40%, more preferably 20% to 35%, and even more preferably 25% to 32% of the total fatty acid content, and Cl.sub.8 fatty acids represent from 40% to 90%, preferably from 50% to 80%, and more preferably from 60% to 70% $C_{18}$ of the total fatty acid content.

Preferred lipid formulations also contain less than 35% $C_{14}$ fatty acids or shorter, preferably less than 25%, and more preferably less than 10%.

In terms of chain length, the preferred lipid formulation contains less than 5% fatty acids with $C_{14}$ chains or shorter, 25% to 32% $C_{16}$ fatty acids, and from 60% to 70% $C_{18}$ fatty acid chains.

In terms of their fatty acid contents, lipid formulations for use in the invention may contain: saturated fatty acids in an amount from 20% to 60%, preferably 30% to 55%, and even more preferably 40% to 50%; monounsaturated fatty acids in an amount from 25% to 60%, preferably 30% to 60%, and more preferably 40% to 55%; and polyunsaturated fatty acids in an amount of from 0.5% to 15%, preferably 3% to 11%, and more preferably 5% to 9%.

A particularly preferred lipid formulation for use in the invention comprises 40% to 50% saturated fatty acids, 40% to 50% monounsaturated fatty acid, and 5% to 9% polyunsaturated fatty acid.

The currently preferred lipid formulation for use in the invention has the formula 3% myristic acid, 26% palmitic acid, 15% stearic acid, 40% oleic acid, and 6% linoleic acid as determined by HPLC analysis.

Currently preferred lipids formulations also include animal derived fractionated lipid complexes, one or more hydrogenated vegetable oils, especially olive oil or coconut oil, commercial suppository bases and other lipid formulations or mixtures thereof.

The lipid formulation is useful in the preparation of immunogenic compositions, and in protecting immunogens within the composition from degradation. The lipid formulation is especially useful in maintaining viability of live organisms, particularly bacteria. The lipid formulation acts to maintain the organisms in a live, but dormant state. This is particularly important for vaccines comprising live organisms formulated for oral administration. The lipids also maintain immunogens in a uniform suspension. That is, in the compositions of the invention the immunogenic components, and live organisms in particular, are uniformly distributed throughout a solid or paste like lipid matrix. The lipids also protect the immunogens from destruction by gastrointestinal secretions when orally administered. Protection from macrophage attack is also likely when administered by other routes such as subcutaneously. This allows for uptake of the immunogens and particularly live organisms through the gastrointestinal mucosa, and subsequent replication of organisms in the host. Replication of the live organisms within the host stimulates a protective immune response as determined by a reduction in severity of disease following challenge with virulent bacteria.

Formulations for a wide range of delivery routes may also include additives such as fillers, extenders, binders, wetting agents, emulsifiers, buffing agents, surfactants, suspension agents, preservatives, colourants, salts, antioxidants including mono sodium glutamate (MSG), vitamins such as vitamin E, butylated hydroxanisole (BHA), albumin dextrose-catalase (ADC), protective coatings, attractants and odourants, and agents to aid survival of organisms contained in the lipid but are not limited thereto.

Protective coatings or enterocoatings may be selected, for example, from gels, paraffins, and plastics including gelatin. The coatings further aid in the prevention of exposure to gastric acids and enzymes when the oral administration route is selected.

When used for oral administration, the formulation may also include additives which, for example, improve palatability, such as flavouring agents (including anise oil, chocolate and peppermint), and sweeteners (including glucose, fructose, or any other sugar or artificial sweetener).

The immunogenic component may be a protein, glycoprotein, peptide, or factor with a protein or peptide component, preferably isolated and/or purified, or mixtures thereof. The component may be derived from an agent which may be used to generate an immune response in an animal.

Most usually, the immunogen will bear at least one epitope which is present on an organism which is pathogenic in the animal species to be treated. Other immunogenic structures such as are known in the art may also be used. For example, polysaccharides, glycolipids, and haptens conjugated to a carrier.

Preferably, the immunogenic component is a living organism, preferably a biologically pure culture.

The living organism in the composition may be selected from the group consisting of fungi, protozoans, bacteria and viruses. For example, HIV, SIV, *Brucella* and Anthrax. Preferably the organism is a bacterium. Organisms currently selected from non-pathogenic bacteria are preferred for use in compositions formulated for oral or subcutaneous delivery. A preferred bacterium is a non-pathogenic strain selected from the genus *Mycobacterium* including *M. tuberculosis* complex (comprising *M. tuberculosis, M. bovis, M. africanum* and *M. microtii*), *M. avium-intracellulare* complex (comprising *M. intracellulare* and *M. avium*), *M. paratuberculosis, M. vaccae, M. smegmatis, M. chelonae, M. fortuitum, M. kansasii, M. leprae, M. marinum, M. ulcerans, M. simiae, M. haemophilum, M. malmoense, M. shimoidei, M. gastri, M. terrae* complex, and *M. nonchromogenicum*. In a particularly preferred embodiment the agent is Bacille Calmette Guerin (BCG), an attenuated strain of *M. bovis* including the following strains: 83/6235, Pasteur 1173P2, Glaxo 1077, Japanese 172, Prague, Russian, Brazilian, Danish 1331, Copenhagen, Connaught and including functionally equivalent variants and other attenuated strains of *M. bovis*, clones, mutants and recombinants of these strains either natural recombinants or those produced by any of a wide range of genetic engineering techniques, and antigenic components thereof.

It will be appreciated from the foregoing that the immunogenic component may be a complex of proteins or peptides, or the like.

In one embodiment, the composition includes at least two immunogenic components selected from any of those identified above, and may include multiple combinations of subunit immunogens. Three or more immunogenic components are feasible.

The concentration of the immunogenic component(s) in the composition may vary according to known art protocols provided it is present in an amount which is effective to stimulate an immune response on administration to an animal. In particular, an immune response in the gut associated lymphoid tissue of the small intestine. In the case of mycobacteria a range of from $1\times10^5$ to $1\times10^{10}$ colony forming units (CFU)/ml is appropriate. Preferably, the concentration is from $1\times10^7$ to $1\times10^9$ CFU/ml. For protein and peptide type immunogens a range of from 10-1000 μg per gram of formulation is appropriate. For virus-type immunogens a range of $1\times10^3$ to $1\times10^{10}$, preferably $1\times10^5$ to $1\times10^8$ Plaque Forming Units (PFU)/ml is appropriate. The immune response may be humoral, or cell mediated including a mucosal immune response.

Accordingly, in a further aspect the invention relates to a method for stimulating a mucosal immune response in an animal by administering an immunogenic composition of the invention to the animal.

The composition may be prepared using techniques known in the art. Conveniently, the lipid formulation is heated to liquefy if required, and the immunogenic component(s) and other ingredients (when used) as described above are added. Dispersal of the immunogenic composition may be achieved by mixing, shaking or other techniques that do not adversely affect the viability of the immunogenic component.

Further preferred compositions for use in the invention are also essentially free of aqueous components including water. The term "essentially free" as used herein means that the composition contains less than 10% aqueous components, and preferably less than 5% aqueous components. As indicated above, the presence of components, particularly aqueous solvents, reduces the protective effect of the lipid formulation especially in the gut.

In one embodiment, the immunogenic composition is a vaccine.

In an alternate embodiment, the immunogenic composition is an adjuvant useful for administration with a vaccine to increase efficacy of same. *Mycobacterium*-containing, and BCG-containing antigenic compositions in particular are preferred for use as adjuvants.

Figure 12:
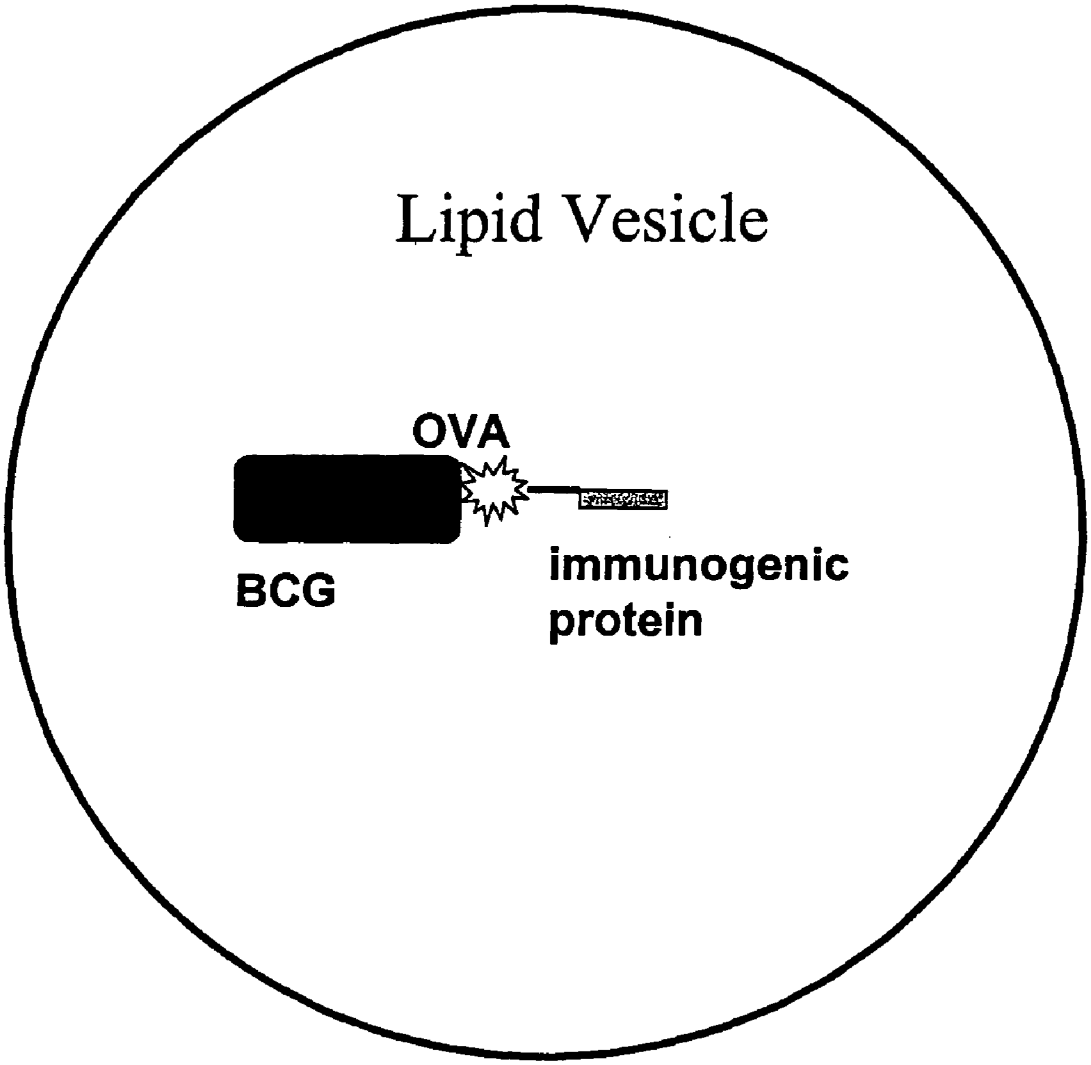
FIG. 12. is a diagram of a generic vaccine delivery system according to the invention.

The immunogenic composition of the invention can also be useful for generating a response to a second or further immunogenic molecule of a type as indicated above for the immunogenic component, particularly those that are weakly immunogenic. This may be achieved by co-delivery of the second or further immunogenic molecule in an immunogenic composition of the invention by conjugating the immunogenic molecule to the immunogen component of the composition. Conjugation may be achieved using standard art techniques (9). In particular, an immunogenic of interest may be conjugated to an immunogenic carrier or adjuvant by a linker group which does not interfere with antibody production in vivo. The immunogenic carrier or adjuvant may be any of the immunogenic components including the organisms identified above but are preferably *Mycobacterium*, and more preferably BCG. Suitable linker groups include mannose receptor binding proteins such as ovalbumin and those that bind to Fc receptors. The second or further immunogenic molecule is preferably a protein or peptide. A particularly preferred protein is an immunocontraceptive protein. The lipid again acts as the delivery matrix. An example of this vaccine delivery system is given in FIG. 12. When the composition is administered an enhanced immune response to the conjugated molecule or co-delivered molecule results.

In a further aspect the invention also provides a method for immunizing an animal, the method comprising administering to said animal an immunogenic composition of the invention.

The term "animal" as used herein refers to a warm-blooded animal, and particularly mammals. Humans, dogs, cats, birds, cattle, sheep, deer, goats, rats, mice, rabbits, possums, badgers, guinea pigs, ferrets, pigs and buffalo are examples of animals within the scope of the meaning of the term. Monogastric and ruminant animals in particular are contemplated within this term.

The compositions of the invention may be administered by a variety of routes including parenteral (subcutaneous, intradermal, intramuscular), mucosal, aerosol and oral administration, but are not limited thereto. In one embodiment, oral administration is preferred. The compositions may be orally administered in the form of pellets, tablets, capsules, lozenges, or other suitable formulations. Oral administration enjoys wide consumer acceptance where the use of needles and syringes can be avoided and is an economical and practical method for vaccinating wildlife. In one embodiment the applicants have therefore provided a novel live vaccine formulated for oral administration.

In an alternate embodiment, the compositions may be formulated for parenteral administration by injection. This form of administration may also include injectable and subcutaneous depot formulations compatible with body tissues. Time release absorption from the depot may be achieved using the lipid formulation alone or with additional biodegradable polymers. The depot allows for sustained release of the immunogenic component in a process which more closely approximates the infection process, facilitating the mounting of an immune response in the animal to which the composition is administered. A lipid protective effect also occurs with these forms of administration.

The composition can be administered as a single dose, particularly for parenteral administration, or in repeated doses over time. For example, an initial dose and booster doses at spaced intervals. The dosage for administration is determined by the release rate of the immunogen component in combination with its immunogenicity. Usual considerations such as weight, age, sex of the animal, concurrent treatments (if any), and nature of the immunogen to be treated may also be taken into account. Generally the dose range for oral vaccination will be as given above, i.e. $1\times10^5$ to $1\times10^{10}$, preferably $1\times10^7$ to $1\times10^9$ CFU/kilogram per dose. For peptide and protein type immunogens the dose range will be from 1-10,000 μg, preferably 10-1000 μg. For virus-type immunogens the dose range will be from $1\times10^3$ to $1\times10^{10}$, preferably $1\times10^5$ to $1\times10^8$ PFU/ml. Whichever method of delivery is used, when live organisms are used in the vaccine formulation they are expected to multiply within the host to facilitate the immune response.

The composition may also be formulated as a single dose preparation or as a multidose preparation for mass vaccination programmes.

Until required for use, the compositions of the invention may be stored for limited periods at room temperature, or preferably under normal refrigeration conditions at approximately 4° C. At 4° C. the lipid formulation facilitates storage and maintenance of organisms in a dormant but viable state without deterioration. For parenteral delivery, the composition is then warmed to 30 to 40° C. to liquefy prior to administration. For oral administration the composition is a solid or a paste.

It will be appreciated that the above description is provided by way of example only and variations in both the materials and techniques used which are known to those persons skilled in the art are contemplated.

Non-limiting examples illustrating the invention will now be provided.

EXAMPLES

Materials and Methods

Bacteria. *M. bovis* BCG Pasteur 1173P2 (Pasteur Institute, Paris) was used as the vaccine strain. The *M. bovis* strain used for macrophage infection studies and for possum challenge was *M. bovis* 83/6235 (AgResearch, Wallaceville, New Zealand) which was originally isolated from a tuberculous lesion in a brushtail possum and has been used in previous macrophage and possum inoculation studies (1, 4). For BCG formulation and macrophage infection, bacteria were grown to mid log phase in 175 ml flasks (Falcon) containing Middlebrook 7H9 medium (Difco, Detroit, Mich.) supplemented with albumin-dextrose-catalase (ADC; BBL, Becton Dickinson, Md., USA). Bacilli were harvested by centrifugation and washed twice in phosphate buffered saline (PBS) prior to storage at −70.degree. C. For possum challenge, *M. bovis* was grown to mid-log phase in between albumin broth (TAB) containing Dubos broth base (Difco Laboratories, Detroit, USA) supplemented with 0.006% v/v alkalinized oleic acid, 0.5% w/v albumin fraction V and 0.25% w/v glucose and the numbers of bacteria were estimated by the degree of turbidity. Dilutions for inoculating the possums were made in TAB. The number of colony forming units (CFU) of BCG or *M. bovis* was determined as described previously (5).

Formulation composition. Three lipid products were selected on the basis of melting temperature and the ability to maintain BCG in uniform suspension for formulating with BCG. Lipids which were liquid at 37° C. but became solid below 30° C. were chosen for testing in BCG viability studies. Following viability testing, the following three formulations were selected for testing in oral vaccine trials in mice and possums: Formulation C—an animal derived fractionated complex lipid; Formulation K—consisting of triglycerides of purified hydrogenated coconut oil; Formulation N—Novarta B, a commercially available suppository base. The three formulations were analysed by gas chromatography to determine the percentage of fatty acid groups.

Formulation of BCG. Pelleted BCG was resuspended in formulation medium which had been warmed to 37° C. BCG was resuspended at a concentration of $1\times10_7$ CFU/ml for vaccination of mice or $1\times10_8$ CFU/ml for vaccination of possums. To increase attractiveness and palatability for possums, 10 mg of glucose and 10 μl of anise oil (Pharmacare, Auckland NZ) were added per ml of formulation. For oral vaccination of mice, 10 mg of glucose, 1 mg of monosodium glutamate (Sigma), and 10% v/v ADC was added per ml of formulation. These additives were dispersed with the formulation lipids and were previously shown not to affect viability of BCG. BCG formulations were transferred to 15 ml tubes (falcon) and allowed to solidify with gentle mixing at 4° C. Formulations were removed from the tubes and aseptically cut into 1 g pellets as required for viability testing and vaccination studies. Pellets were tested for dispersal of BCG by culturing on 7H11 agar plates and counting CFU as described below.

BCG viability. The number of CFU in the formulations following storage at 4° C. or at room temperature (10-25° C.) was determined as described previously (4). Samples for culture were collected by warming 100 mg aliquots of the three BCG formulations to 37° C. for 15 min and performing serial 10-fold dilutions in 7H9 broth. Numbers of viable organisms were determined by inoculating 100 μl of each emulsion onto Middlebrook 7H11 agar plates (Difco) supplemented with oleic acid-ADC (OADC; Becton Dickinson) and 0.5% glycerol. Emulsions were dispersed using a glass spreader. Plates were sealed with parafilm and incubated in 5% $CO_2$ at 37° C. The number of colonies was counted after 2-3 weeks of culture. Results are expressed as CFU/μg of BCG formulation.

Vaccination of mice. Specific pathogen free female BALB/c mice (6-8 weeks old) were obtained from the University of Otago Department of Animal Laboratory Sciences, Dunedin. Mouse experiments were conducted under ethics approval from the University of Otago Animal Ethics Committee (Approval No: 51/2000). Mice were separated into individual cages and taken off food for 12 h prior to oral vaccination. Non-formulated controls consisted of *M. bovis* BCG in Craig's preservative-free strawberry jam (Heinz-Watties Ltd., Hastings, New Zealand). A previous study had shown that *M. bovis* BCG viability over a 24 h interval was not affected by mixing *M. bovis* BCG in the jam (data not shown). Non-vaccinated controls consisted of lipid formulation alone. For dose response and time course experiments mice were given vaccine in two separate doses at 24 h intervals. For aerosol challenge experiments, mice were given a single oral dose ($5\times10^7$ CFU) or vaccinated subcutaneously with $1\times10^6$ CFU. The mice were observed at various intervals during consumption of pellets and jam to ensure the full dose was eaten. At various time-points post vaccination, the mice were sacrificed by $CO_2$ inhalation and their spleens were removed aseptically.

Spleen cell proliferation assay. Spleen cell suspensions were prepared by filtering cells through a cell strainer (70-μm mesh; Beckton Dickinson). Erythrocytes were lysed in 0.83% $NH_4Cl$ (pH 7.2). Cells were washed twice in PBS and resuspended to $1\times10^6$/ml in Dulbeccos's modified Eagles medium (DMEM) containing 10% foetal calf serum (FCS), 20 mM HEPES penicillin at 100 U/ml, streptomycin at 100 μg/ml, $5.5\times10^{-5}$ M 2-mercaptoethanol (DMEM-10% FCS; all from Gibco-BRL, USA). Cells were resuspended to a concentration of $10^7$ per ml in RPMI plus 10% foetal calf serum (Gibco). Splenocytes ($5\times10^5$ per well) were plated out in triplicate wells in 96-well plates (Nunc). Cells were cultured with purified protein derivative from a culture of *M. bovis* (bovine PPD; CSL, Melbourne, Australia), 60 μg/ml final concentration or with medium alone. Cells were harvested 4 days later, after an 18-h pulse with 1 μCi of [$^3$H] thymidine (Amersham, Buckinghamshire, England)), and the incorporated thymidine was measured as previously described (5). A stimulation index (SI) was obtained by dividing the mean counts per minute (cpm) for the triplicate cultures incubated with bovine PPD by the mean cpm for splenocytes cultured with medium only.

In vitro assay for cytokine production by spleen cells. Spleen cell suspensions were prepared as described above for the spleen cell proliferation assay. One ml of cell suspension was dispensed into 24 well plates (Costar) and 100 μl of either PBS or bovine PPD (60 μg/ml final concentration) was added to the wells. Cultures were incubated for 72 h in 5% $CO_2$ at 37° C. after which time 200 μl of culture supernatant was collected and frozen at 70° C. for cytokine analysis. Interleukin-2 (IL-2) and interferon-gamma (IFN-γ) capture ELISAs were performed according to the manufacturers instructions using a commercial kit (R&D Systems, Duoset, City, Country) Cytokine levels in culture supernatants were quantified by extrapolation from standard curves. The minimum sensitivities of the two ELISAs were determined to be 50 pg/ml for IFN-γ and 35 pg/ml for IL-2.

*M. bovis* inhibition assay. Peritoneal-derived macrophages were tested for inhibition of intracellular growth of *M. bovis* following co-culture with or without autologous lymphocytes. Experiments were performed according to a modification of previously described protocols. Peritoneal exudate cells (PEC) were obtained by lavage from female BALB/c mice. Cells were collected in PBS supplemented with 1% BSA and 20 U/ml of heparin, washed once and resuspended in DMEM medium containing 10% foetal calf serum and 100 U/ml penicillin (supplemented DMEM) at $2\times10^6$/ml. 100 μl of cell suspension was dispensed into a 96 flat well plate (Nunc). After incubation for 2 h in 5% $CO_2$ at 37° C. the nonadherent cells were removed, washed and resuspended at a density $5\times10^6$/ml in supplemented DMEM. Nonadherent cells were selectively depleted of the remaining adherent population by incubation in 25 ml flasks (Falcon). Nonadherent PEC (NPEC) were determined to comprise >90% lymphocytes following May-Grunwald/Giemsa staining. Warm supplemented DMEM was added to the adherent monolayer which was estimated to contain $5\times10^4$ cells/well. This population was found to be 98% positive with a non-specific esterase staining kit (catalogue no. 181-B; Sigma, St. Louis, Mo., USA) and is henceforth referred to as macrophages. Macrophages were infected with *M. bovis* at an MOI of 2 bacilli per macrophage as described previously (2). Non phagocytosed bacteria were removed by gentle washing. One hundred μl (containing $5\times10^5$ cells) of autologous NPEC was added to each well containing infected macrophages and cultures were further incubated in 5% $CO_2$ at 37° C. The resulting 10:1 NPEC-to-macrophage ratio was selected to approximate that of the ratio found in peripheral blood mononuclear cells. Control wells consisted of *M. bovis*-infected macrophages alone or uninfected NPEC and macrophages. After 72 h, cells were pulsed with 1.0 μCi [$^3$H]uracil for 18 h. The cells were lysed with 0.1% saponin and the bacteria heat killed at 80-90° C. for 20 minutes prior to harvesting onto glass fibre filters (Whatman Inc, Finland) using an automated cell harvester (Cambridge Technology, USA). The amount of [$^3$H]uracil incorporated was determined using a liquid 13-scintillation counter (Wallac, 1205 betaplate scintillation counter (Pharmacia, UK)).

Aerosol challenge of mice with *M. bovis*. Six mice per vaccine group were challenged by aerosol with virulent *M. bovis* 8 weeks after vaccination. A single cell suspension of *M. bovis* 83/6235 was prepared using a modification of a method described by Grover et al., 1967 and stored at −70 C. For preparing these suspensions, the bacterial cells were dispersed by sonication for 30 seconds and filtered through an 8 μM membrane filter. Mice were infected via the respiratory route using an aerosol chamber which produces droplet nuclei of the size appropriate for entry into alveolar spaces. The concentration of viable *M. bovis* in the nebulizer fluid was empirically adjusted to result in the inhalation and retention of 5-20 viable organisms per mouse lungs (B. Buddle and G. de Lisle, unpublished data). A similar procedure has been shown to result in reproducible, uniform infection of the lungs of guinea pigs. The aerosol infection and subsequent maintenance and manipulation of infected mice were performed under strict isolation conditions in a biohazard facility.

Isolation of *M. bovis*. Mice were euthanased between 37 and 40 days after aerosol challenge. The lungs and spleen from each mouse were processed individually for mycobacterial isolation. The organs were homogenized in a Ten-Broeck grinder and samples centrifuged at 3500 g for 20 min. The deposits were resuspended in 1 ml of distilled water. Appropriate dilutions were made in TAB and a 0.1 ml volume of a diluted or undiluted sample was inoculated onto a modified mycobacteria 7H11 agar (1). Two replicates were prepared for each dilution. Culture conditions and methods for identification of isolates were carried out as previously described (1)

Analysis of Data

Statistically analyses of differences in the mean cytokine levels and $\log_{10}$ transformed spleen cell proliferation responses for the vaccine groups were determined using the Student t test. The bacterial counts from the lung and spleen were $\log_{10}$ transformed and analysed using analysis of variance. For statistical purposes, when no bacteria were cultured from tissues, half the lowest detectable count (% CFU/organ) was used.

Vaccination and challenge of possums. Possums were trapped and housed as previously described (4). BCG was fed to two groups of possums (5 animals/group). A 1 g pellet of formulated BCG ($1\times10^8$ CFU) was given to each possum in one group. A second group was given BCG ($1\times10^8$ CFU) in jam to control for the formulation procedure. The jam had previously been shown not to inhibit BCG viability (data not shown). A third group (6 animals/group) was given pellets containing formulation medium only and served as non-vaccinated controls. Possums were observed during consumption of pellets to ensure the full pellet was eaten. The following day the vaccinations were repeated (total BCG dose $2\times10^8$ CFU/possum). All of the possums were challenged by the aerosol route 41 days after vaccination. In a second experiment, four oral lipid BCG formulations were compared with subcutaneous vaccination. Six possums per vaccine group were challenged by aerosol with virulent *M. bovis* 8 weeks after vaccination using lipids C, K, N and F (a modification of K containing 10% foetal calf serum)

Aerosol challenge of possums with *M. bovis*. The possums were challenged with *M. bovis* 83/6235, which was originally isolated from a lymph node of a possum from Taumaranui, New Zealand (5). Single cell suspensions of the isolate were prepared using a modification of a method described by Grover et al., 1967 and stored at −70° C. For preparing these suspensions, the bacterial cells were dispersed by sonication for 30 seconds and filtered through an 8μ membrane filter. Possums anaesthetized with an intramuscular injection of ketamine HCl (30 mg/kg; Parnell Laboratories, Auckland, New Zealand) were infected via the respiratory route by using an aerosol chamber which produces droplet nuclei of the size appropriate for entry into alveolar spaces. The concentration of viable *M. bovis* in the nebulizer fluid was empirically adjusted to result in the inhalation and retention of 10-20 viable organisms per possum (Buddle and de Lisle, unpublished). This challenge dose had previously been estimated from the number of primary tubercles observed grossly in the lungs of non-vaccinated possums at 4 weeks post-infection. A similar procedure has been shown to result in reproducible, uniform infection of the lungs of guinea pigs (Wiegeshaus et al., 1970; Smith et al., 1970). The aerosol infection and subsequent maintenance and manipulation of infected possums were performed under strict isolation conditions in a biohazard facility.

Necropsy of possums. All possums were killed between 56 and 57 days after challenge and subjected to extensive gross post-mortem examination. The lungs were separated from surrounding tissues and weighed.

Isolation of *M. bovis* from possum tissues. From each animal, a sample of lung and spleen each weighing approximately 1 g, was taken from a macroscopic lesion, or, if no lesion was present, a sample was taken from a pre-determined part of the organ and processed individually for mycobacterial isolation. Samples were weighed, homogenized in a Ten-Broeck grinder and decontaminated in 0.75% cetyl-pyridinium chloride for 1 h. Samples were centrifuged at 3500 g for 20 min and deposits resuspended in 1 ml of distilled water. Appropriate dilutions were made in TAB and a 0.1 ml volume of a diluted or undiluted sample was inoculated onto a modified mycobacteria 7H11 agar plate. Two replicates were prepared for each dilution. Culture conditions and methods for identification of isolates were carried out as previously described (1).

Possum peripheral blood lymphocyte proliferation assay. Proliferative responses to PPD-B and PPD-A (CSL Limited, Parkville, Australia) were measured using whole blood depleted of red blood cells. Responses to Con A were also tested. Briefly, 1 ml of heparinized blood was mixed with 50 ml 0.17 M Tris-0.16 M $NH_4Cl$, pH 7.2 at 37° C. for 10 min, washed twice in PBS at 20° C. and made up to 3 ml in DMEM tissue culture medium supplemented with 2 mM glutamine and 2% normal possum serum. The cells (200 μl) were plated into flat bottom 96 well plates containing 50 μl PPD-B, PPD-A or Con A in PBS or PBS alone to give final concentrations of 60 μg/ml PPD or 5 μg/ml Con A. Plates were placed in a 5% $CO_2$ in air incubator for 72 hr, pulsed with 1 μCi/well $^3$H-tritiated thymidine (Amersham, UK), harvested after a further 18 h and $^3$H counted in a Micro Beta Trilux (Wallac, Finland). The stimulation index (SI) was calculated by dividing counts per minute (cpm) from triplicate cultures stimulated with PPD by cpm from triplicate cultures with medium and PBS.

Analysis of Data

Statistically significant differences of mouse cytokine secretion were determined using the Student t test (GraphPad, San Diego, Calif.). These studies were performed twice with similar results. For possum lymphocyte proliferation responses, stimulation indices of >3.5 were scored as a positive response as this represents a response at least three standard deviations above the mean of the background (mean SI for PPD-B prior to vaccination). The possum body weight changes, lung weights, lymphocyte blastogenic responses and bacterial counts for the different treatment groups were initially compared by one-way analysis of variance. Duncan's multiple range test was then used to compare the means for individual groups. Lymphocyte proliferation responses and bacterial counts from the lung and spleen were $\log_{10}$ transformed prior to analysis. For statistical purposes, when no bacteria were cultured from tissues, half the lowest detectable count (5 CFU/g tissue) was used.

Results

A. Fatty acid composition of formulation lipids. Lipids selected for use in formulating oral BCG were analysed by gas chromatography. FIG. 1 shows the fatty acid composition of the 3 lipids used in mice and possum vaccination trials.

The relative percentage of fatty acids in the three lipid formulations are shown in FIG. 1. Chemical analysis of lipids by HPLC showed that the 3 formulations comprised the following mixtures of fatty acids:

Formulation C.

89% total lipid (48.5% neutral, 40.5% polar-comprising 3% myristic acid, 26% palmitic acid, 15% stearic acid, 40% oleic acid and 6% linoleic acid), Formulation K 47% lauric acid, 20% myristic acid, 12% palmitic acid, 12% stearic acid and 3% oleic acid.

Formulation N. Novarta B, a commercially available suppository base consisting of a mixture of esterified, hydrogenated, fractionated vegetable oils with synthetic triglyceride mixtures. comprising: 44% lauric acid, 20% myristic acid, 16% palmitic acid, 19% stearic acid.

B. BCG Viability Following Formulation.

Figure 2A:
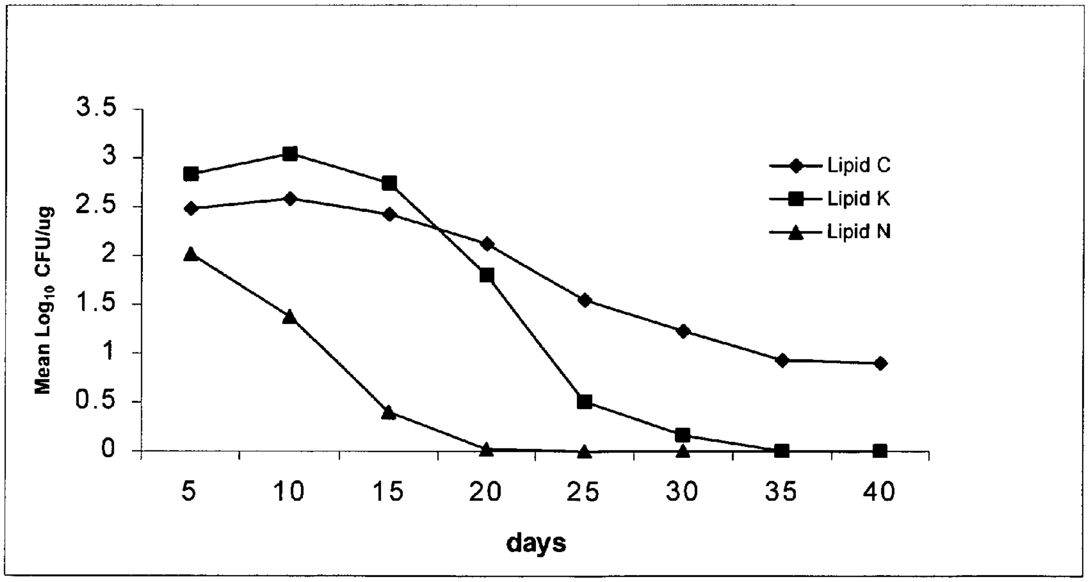
FIG. 2. BCG viability following formulation and storage in lipids at 4° C. (2*a*) or room temperature (10-25° C.) (2*b*). BCG formulations were warmed to 37° C. and emulsified in 7H9 broth. Numbers of viable organisms were determined by inoculating serial 10 fold dilutions of each emulsion onto 7H11 agar plates. The number of CFU/ul of formulation media was determined after 2-3 weeks of culture. Results are representative of duplicate experiments and are expressed as means.

The viability of formulated BCG following storage at 4° C. is shown in FIG. 2*a*. Over a period of 16 weeks, formulations C and K maintained high levels of BCG viability with formulation C showing higher retention of viability (98%) compared to formulation K (52%). In contrast, formulation N showed a progressive loss of BCG viability resulting in greater than 97% loss of viable organisms by 16 weeks. These results suggest that formulations C and K are more suited to maintaining BCG viability at 4° C. compared to formulation N.

Figure 2B:
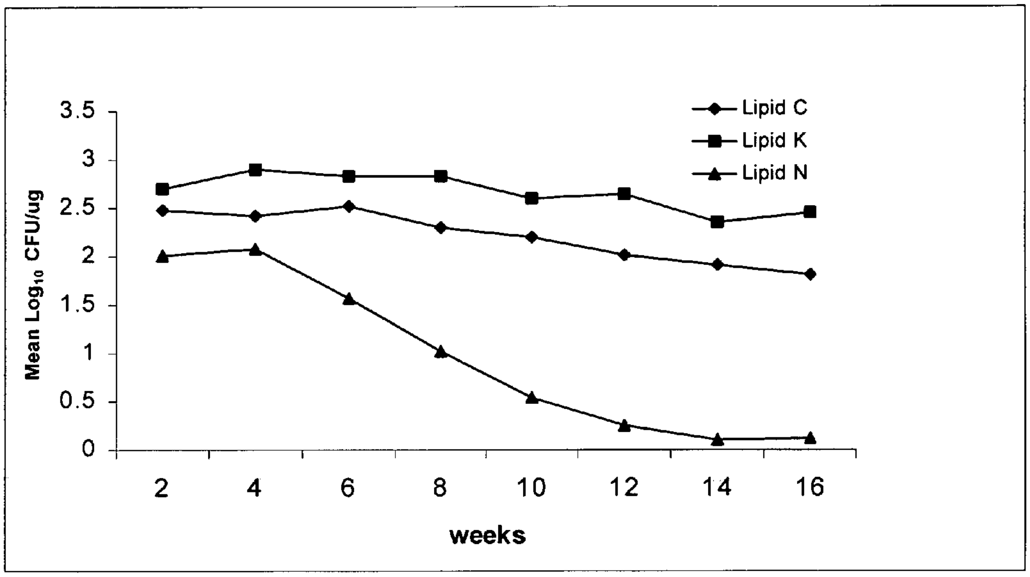

The viability of formulated BCG following storage at room temperature (10-25° C.) is shown in FIG. 2*b*. Formulations C and K maintained high levels of BCG viability with formulation C showing prolonged retention of viability (mean logio CFU/ug=10) at 40 days compared to formulation K (mean logio CFU/ug=10) at 22 days In contrast, formulation N showed a rapid loss of BCG viability (mean logio CFU/ug=10) at 12 days. These results suggest that formulations C and K are more suited to maintaining BCG viability at room temperature compared to formulation N.

C. Immunogenicity of Formulated BCG in Mice.

Oral delivery of formulated *M. bovis* BCG induces immune responses in mice. To determine a suitable method of measuring systemic immune responses following oral delivery of *M. bovis* BCG, we compared bovine PPD-induced splenocyte proliferation (LTA), and splenic IL-2 and IFN-γ responses at 8 weeks following oral delivery of $10^7$ CFU of lipid-formulated *M. bovis* BCG or *M. bovis* BCG in jam (non-formulated *M. bovis* BCG). Table 1 shows that while both the LTA and IFN-γ assays showed significant differences between the formulated and non-formulated oral *M. bovis* BCG groups, the differences for the IL-2 assay were not significant. The IFN-γ assay was used in further experiments to monitor systemic immune responses due to importance of IFN-γ in protection against tuberculosis.

Figure 3:
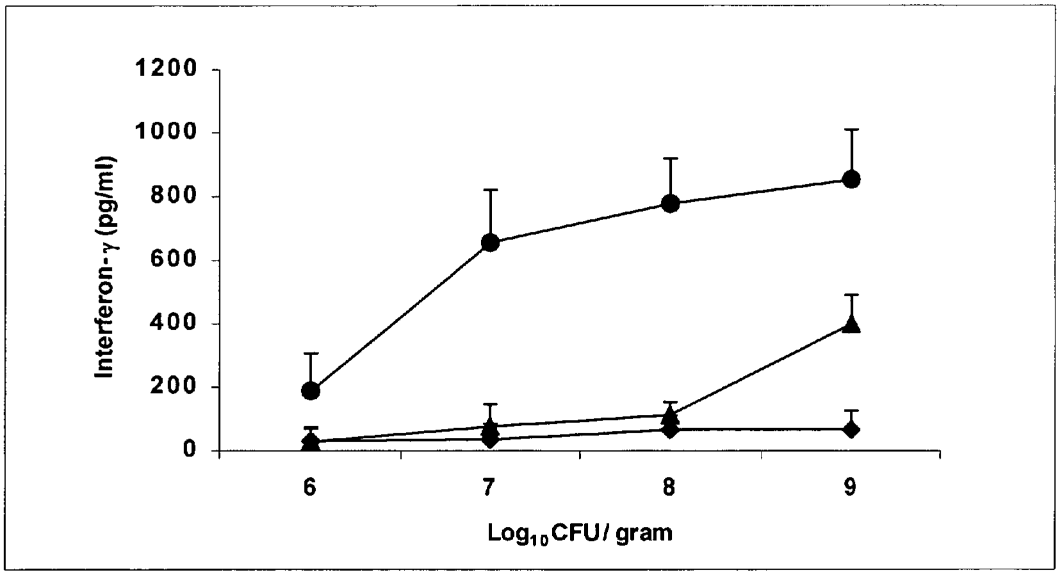
FIG. 3. Bovine PPD induced IFN-γ responses following oral vaccination with varying doses of formulated *M. bovis* BCG. Mice were sacrificed at 8 weeks after oral immunization with formulated *M. bovis* BCG (circles), non-formulated *M. bovis* BCG (triangles) or formulation material only (diamonds). Splenocytes were incubated with bovine PPD for 72 h. Supernatants were then collected and analysed using a sandwich ELISA. Each treatment group contained 6 mice. Spleens were individually processed. Results are expressed in pg/ml and are presented as means of triplicate determinations. Bar indicates standard error.
Figure 4:
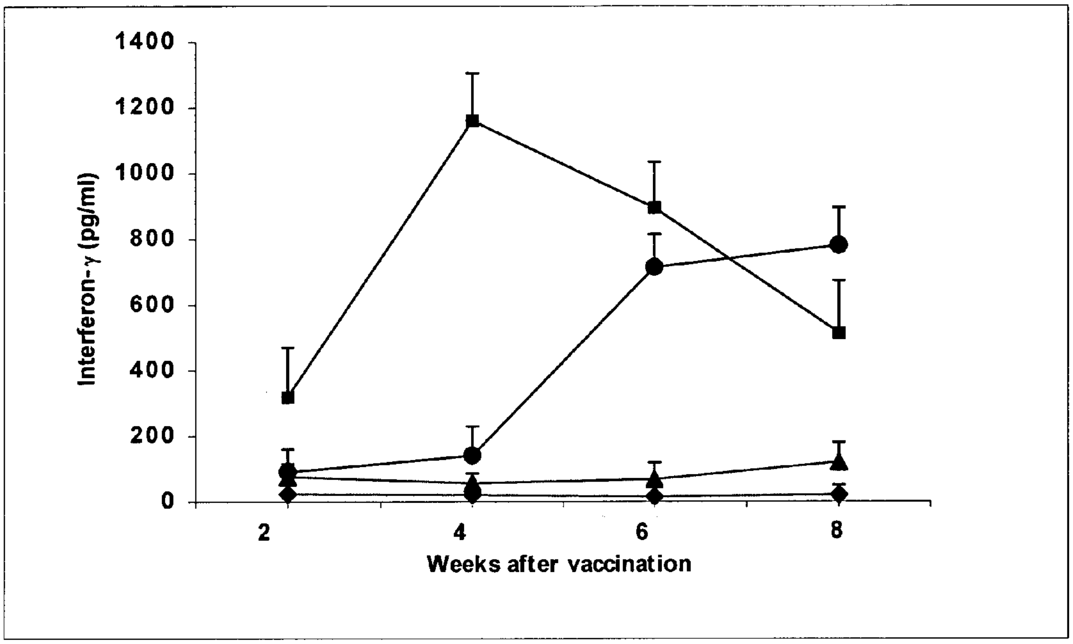
FIG. 4. Antigen-induced splenic IFN-γ responses to *M. bovis* BCG vaccination in BALB/c mice. Mice were euthanased at 2, 4, 6 and 8 weeks after vaccination with $10^6$ CFU subcutaneous *M. bovis* BCG (squares), oral delivery of $10^7$ CFU of formulated *M. bovis* BCG (circles), non-formulated *M. bovis* BCG (triangles), or formulation material only (diamonds). Splenocytes were incubated with bovine PPD for 72 h. Supernatants were then collected and analysed using a sandwich ELISA. Each treatment group contained 5-6 mice. Spleens were individually processed. Results are expressed in pg/ml and are presented as means of triplicate determinations. Results at 8 weeks are from 2 separate experiments. P value $<0.05$ (Student t test). Bar indicates standard error.

To determine the effect of dose of *M. bovis* BCG following oral delivery, we compared splenic IFN-γ responses to bovine PPD in mice vaccinated with varying doses of formulated or non-formulated *M. bovis* BCG at 8 weeks post vaccination. FIG. 3 shows that a low level of IFN-γ (<200 pg/ml) was detected in the formulated group following oral immunization with $10^6$ CFU of *M. bovis* BCG, but there were no significant differences between the vaccine groups. When the dose was increased to $10^7$ CFU, IFN-γ responses in the non-formulated group remained low whereas responses to formulated *M. bovis* BCG increased significantly (P<0.05). Similar differences were seen with $10^8$ CFU of *M. bovis* BCG. When the vaccine dose was increased to $10^9$ CFU of BCG, an increase in the levels of IFN-γ was seen in the non-formulated group while the formulated group remained high. At doses of *M. bovis* BCG ranging from $10^7$-$10^9$ CFU, IFN-γ responses in the formulated *M. bovis* BCG group were significantly greater that those of non-formulated *M. bovis* BCG. The increase in IFN-γ responses seen at the high dose in the non-formulated group shows that considerably higher doses of oral *M. bovis* BCG are required for induction of immune responses compared to formulated *M. bovis* BCG. To determine the time course of immune responses to oral *M. bovis* BCG, we compared splenic IFN-γ responses at 2 weekly intervals following oral or subcutaneous vaccination with *M. bovis* BCG. FIG. 4 shows that IFN-γ responses following subcutaneous vaccination peaked at 4 weeks and gradually declined at weeks 6 and 8. By comparison, IFN-γ responses following oral vaccination with formulated *M. bovis* BCG first increased at 6 weeks and remained high at 8 weeks post vaccination. IFN-γ responses to non-formulated *M. bovis* BCG or formulation material alone remained low between 2 and 8 weeks. These results show that immune responses following oral vaccination with formulated *M. bovis* BCG are delayed compared to subcutaneous vaccination but appear to persist at least to 8 weeks.

Figure 5:
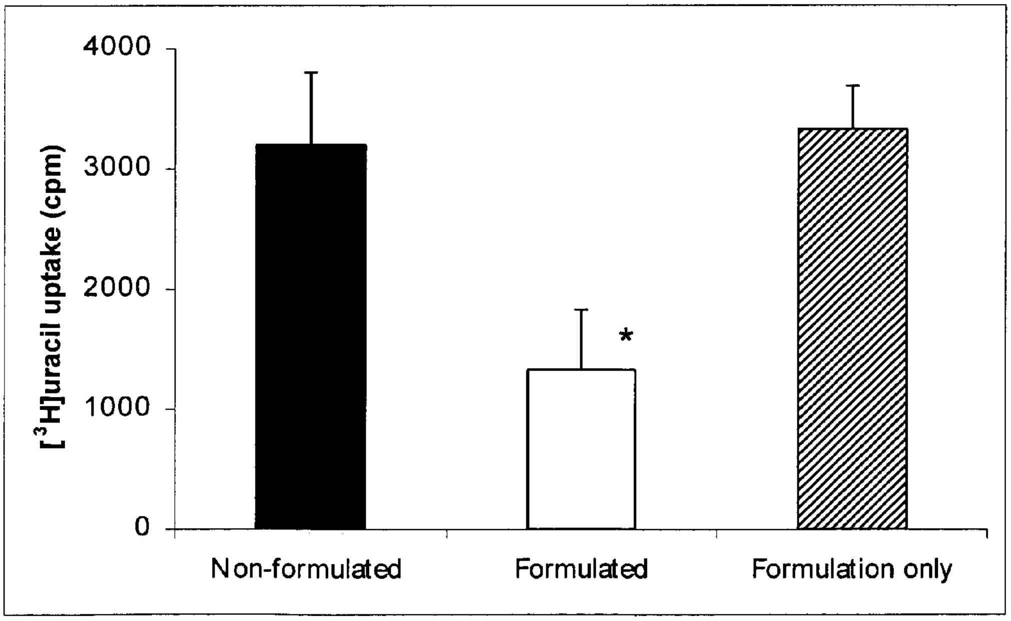
FIG. 5. Growth inhibition of *M. bovis* by macrophages co-cultured with nonadherent peritoneal exudate cells (NPEC). Macrophages were infected with *M. bovis* at an MOI of 2 bacilli per macrophage. Non-adherent autologous NPEC were added at a ratio of 10 NPEC per macrophage. [$^3$H]uracil incorporation was then assessed at 72 h post infection. The mean [$^3$H]uracil uptake by cell cultures which did not contain *M. bovis* was 460 cpm. Growth of intracellular bacilli from co-cultured macrophages and NPEC was expressed as means of triplicates. The results are representative of two experiments. *Represents a mean which is significantly different from the mean of Formulation only control group; bar indicates standard error.

Peritoneal-derived lymphocytes from mice orally vaccinated with formulated *M. bovis* inhibit growth of *M. bovis* in autologous macrophages. The addition of NPEC to *M. bovis*-infected macrophages from mice vaccinated with oral *M. bovis* BCG formulations was performed in order to determine whether lymphocyte-mediated effector mechanisms could inhibit intracellular growth of *M. bovis*. Growth of *M. bovis* in macrophages was determined by [$^3$H]uracil uptake. The growth of *M. bovis* within macrophages alone or when co-cultured with NPEC from orally vaccinated mice is illustrated in FIG. 5 Macrophages prepared from mice orally vaccinated with formulated or non-formulated *M. bovis* BCG or mice given formulation material alone showed no differences in their ability to control *M. bovis* growth. When NPEC from mice vaccinated with formulated *M. bovis* BCG were co-cultured with autologous *M. bovis*-infected macrophages, the [$^3$H]uracil counts were significantly reduced compared to co-culture of NPEC from mice vaccinated with non-formulated *M. bovis* BCG or formulation material alone (P<0.05). These results demonstrate that lymphocytes from mice orally vaccinated with formulated *M. bovis* BCG activate macrophages to inhibit intracellular growth of *M. bovis*. Control of intracellular growth of *M. bovis* in vitro may reflect growth inhibition in vivo leading to reduced dissemination of *M. bovis* in the host.

Oral vaccination with formulated *M. bovis* BCG protects against aerosol challenge with virulent *M. bovis*. In order to determine the protective efficacy of formulated oral *M. bovis* BCG, mice were orally vaccinated with 5×$10^7$ CFU formulated *M. bovis* BCG or subcutaneously vaccinated with 1×$10^6$ CFU *M. bovis* BCG. Non-vaccinated mice served as controls. Mice were challenged with virulent *M. bovis* by the aerosol route 8 weeks after vaccination and euthanased 37-40 days after challenge. Table 2 shows that subcutaneous *M. bovis* BCG vaccination reduced the bacterial lung count by approximately 2.34 logs and the bacterial spleen count by 1.90 logs. By comparison, formulated oral *M. bovis* BCG reduced the bacterial lung count by approximately 1.0 log and the bacterial spleen count by 1.48 logs. The results in Table 2 showed that oral formulated *M. bovis* BCG and subcutaneous *M. bovis* BCG induced significant protection against aerosol challenge with virulent *M. bovis*, although the protective efficacy of subcutaneous *M. bovis* BCG in the lung was greater than that for oral formulated *M. bovis* BCG group.

D. Immune Responses and Pathology in Possums.

Figure 6:
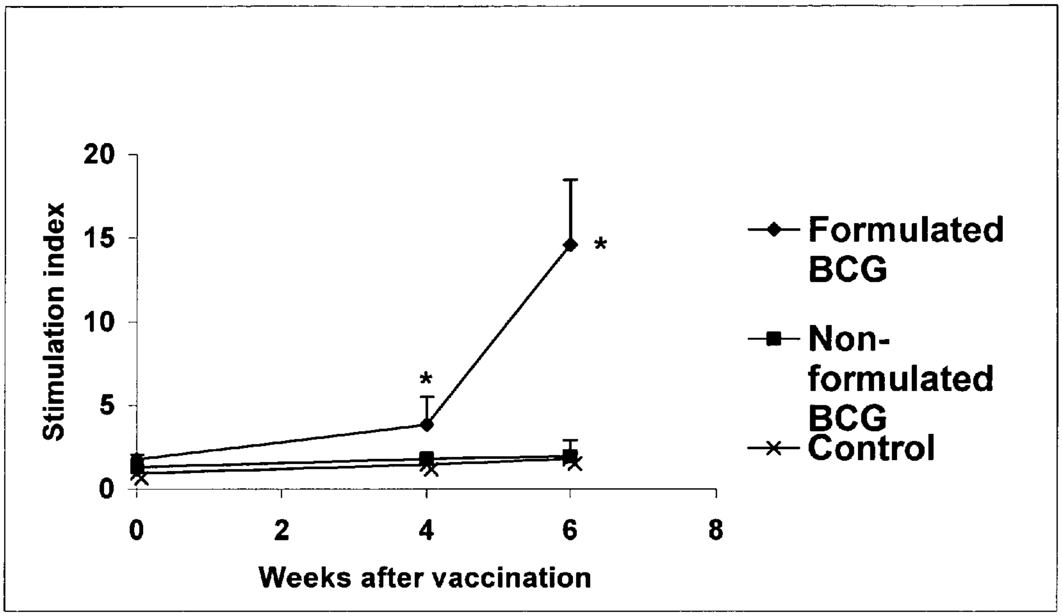
FIG. 6. Effect of oral vaccination of possums with formulated BCG on in vitro peripheral blood lymphocyte blastogenic responses to PPD-B. Formulated BCG -♦-; non-formulated BCG, -■- ; non-vaccinated control -X-; Results are expressed as mean stimulation index (SI). *Represents a mean which is significantly different from the mean of non-vaccinated control group. Bar indicates SE.

Lymphocyte blastogenic responses. The effect of oral vaccination with formulated BCG on the whole blood lymphocyte blastogenic responses to bovine PPD is shown in FIG. 6 and Table 3. At 6 weeks after vaccination, the mean stimulation indices (SIs) to PPD-B for the formulated BCG group were significantly higher than for non-formulated BCG and non-vaccinated control groups (P<0.05). At 4 weeks following challenge with *M. bovis* all groups showed a mean SI for PPD-B of >20. These results show that oral delivery of formulated BCG elicits strong immune responses to PPD-B in possums compared to non-formulated BCG.

Figure 11:
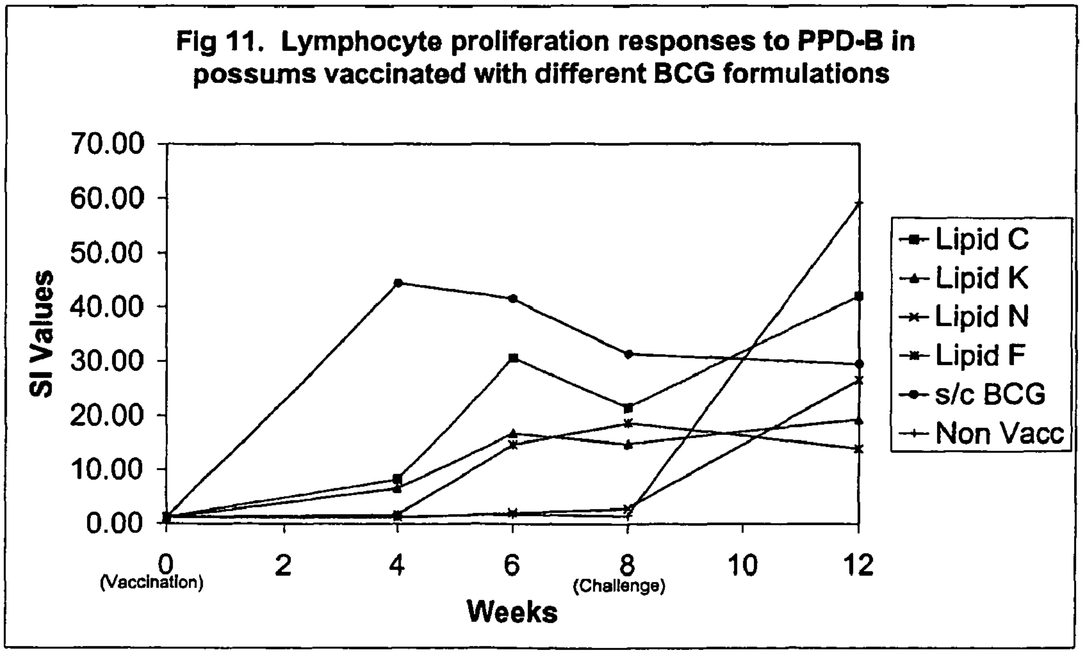
FIG. 11. Comparison of immune responses to four oral lipid BCG formulations or to subcutaneous vaccination. The figure shows the effect on in vitro peripheral blood lymphocyte blastogenic responses to PPD-B in possums following vaccination (week 0) and challenge (week 8). Results are expressed as mean stimulation index (SI).

A further experiment compared immune responses to four oral lipid BCG formulations with subcutaneous vaccination (FIG. 11), Subcutaneously vaccinated possums showed strong LTA responses which peaked at 4 weeks post vaccination (Mean SI 42.5) and gradually dropped to SI=30 by 8 weeks In contrast, Lipid N formulated oral BCG failed to elicit an LTA response during the 8 week vaccination period. Oral BCG formulated in lipids C, K and F induced LTA responses which were weak (SI=1-7) at 4 weeks post-vaccination but increased progressively and were sustained through to 8 weeks post-vaccination (SI=15-22). These results show that systemic immune response to oral vaccination is delayed compared with subcutaneous vaccination but that they may persist longer. Formulation N did not induce LTA responses above those seen with the non-vaccinated possums nor did it protect against aerosol challenge with *M. bovis* (see Table 4), an indication that the type of lipid used to formulated oral BCG is important for protection against tuberculosis.

Figure 7:
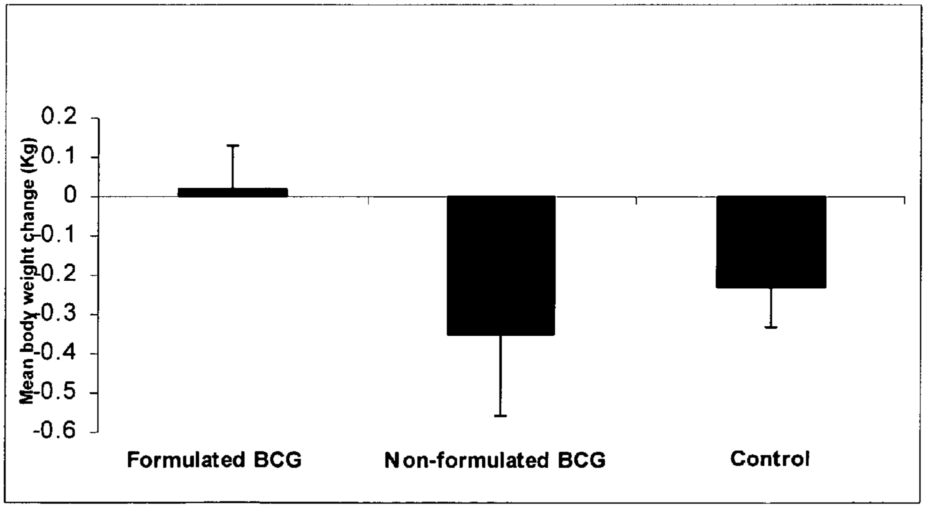
FIG. 7. Effect of oral vaccination with formulated BCG on body weight of possums challenged with *M. bovis*. Mean body weight change was determined over the period from challenge to necropsy. The mean body weight of the possums immediately prior to challenge was 3.0±0.07 (±SE) kg. Bar indicates SE.

Clinical findings. The mean body weight changes between challenge and necropsy for the different groups are shown in FIG. 7. The mean body weight of possums vaccinated with formulated BCG increased by 0.02 kg between the time of challenge and necropsy. In contrast, the mean body weights for the non-formulated BCG and non-vaccinated control groups decreased by 0.35 kg and 0.23 kg respectively during this period. However these differences were not statistically significant.

In a further experiment (Table 4), which compared four oral lipid BCG formulations with subcutaneous vaccination, the mean body weight changes between challenge and necropsy were significantly reduced for the subcutaneous vaccination group (mean weight loss 0.012 kg) and one of the oral lipid BCG groups (group F) (0.035 kg) compared to the non-vaccinated group (0.147 kg). By comparison, the mean weight loss for the remaining oral BCG groups were 0.060 kg (lipid C), 0.067 kg (lipid K) and 0.122 kg (lipid N). Possums which did not show an immune response to vaccination (ie non-vaccinated and lipid N groups) showed greater body weight loss compared with those that responded.

Figure 8:
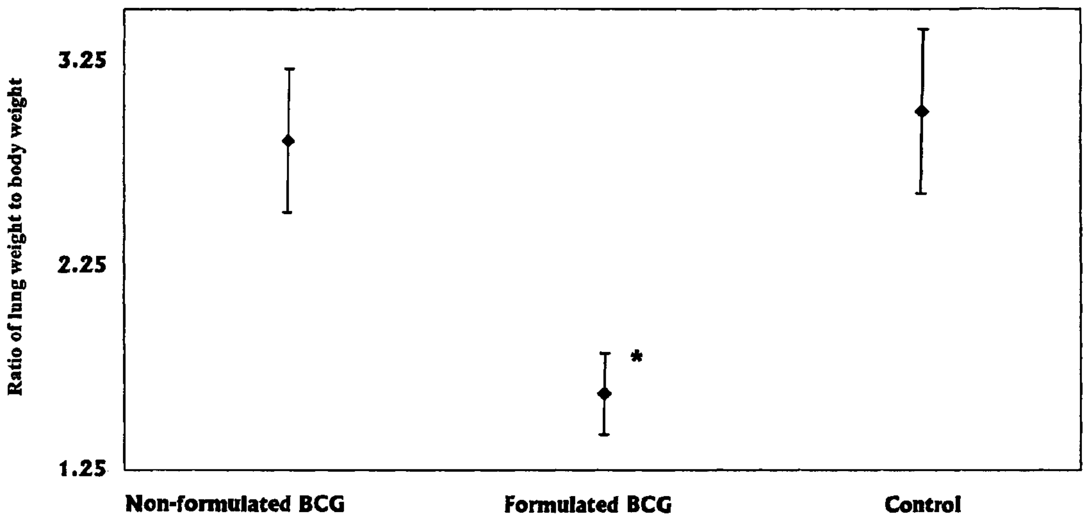
FIG. 8. Effect of oral vaccination with formulated BCG on lung weight of possums challenged with *M. bovis*. Mean lung weight was determined at necropsy. In order to standardize differences in lung weight with variation in body weight, the lung weight of each animal was compared with the body weight and expressed as a ratio. *Represents a mean which is significantly different from the mean of non-vaccinated control group; bar indicates SE.

Pathology. Macroscopic lesions were observed in the lungs of all of the challenged animals. The extent of tuberculous pneumonia can be estimated from the lung weights (FIG. 8). High lung weight is associated with extensive tuberculous pneumonia (3) (4). In order to standardise differences in lung weight with variation in body weight, the lung weight of each animal was compared with the body weight and expressed as a ratio. The ratio of mean lung weight to body weight of the animals vaccinated with formulated BCG was 1.62. By comparison the ratio of mean lung weight to body weight of the non-formulated BCG and non-vaccinated control groups were 2.86 and 3.0 respectively. The lung weight to body weight ratio of the possums vaccinated with formulated BCG was significantly different from the non-formulated BCG and non-vaccinated control groups ($P<0.05$). Typically, the lung lesions were small consolidated areas or lobar consolidation with a yellow necrotic area in the centre of the lesion. Swollen bronchial lymph nodes were observed in animals with the most extensive lung lesions.

In the second experiment (Table 4) which compared four oral lipid BCG formulations with subcutaneous vaccination, there were no significant differences in the ratio of mean lung weight to body weight between the vaccination groups. However possums which did not show an immune response to vaccination (ie non-vaccinated and lipid N groups) had higher mean lung weights compared with those that responded.

Bacteriology

Figure 9:
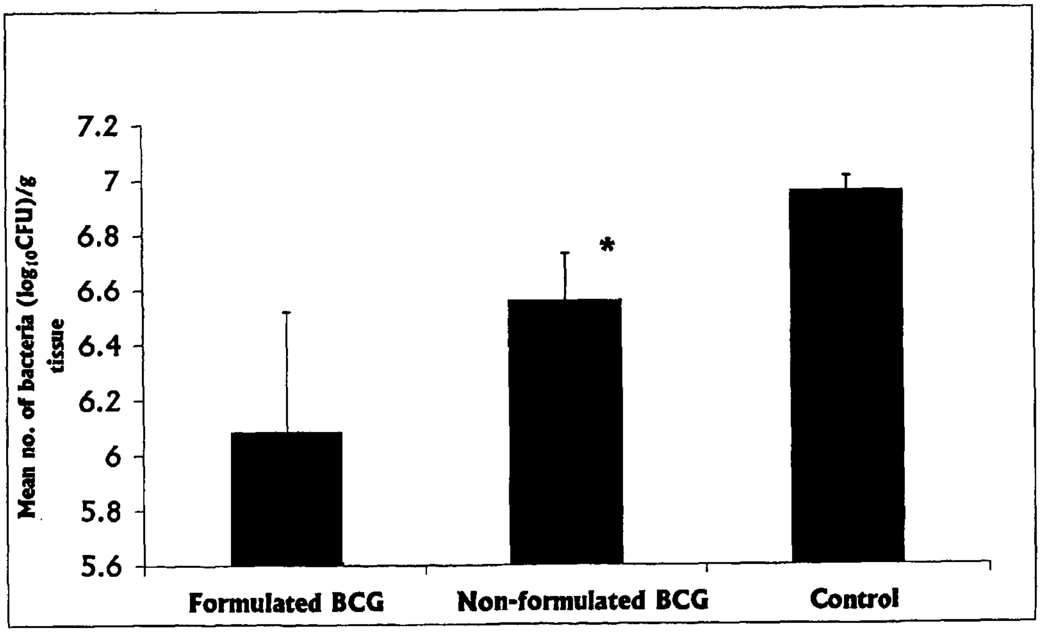
FIG. 9. Effect of oral vaccination of possums with formulated BCG on mean numbers of mycobacteria isolated from lungs following challenge with *M. bovis*. Results are expressed as the geometric mean number of CFU ($\log_{10}$)/g of tissue. *Represents a mean which is significantly different from the mean of non-vaccinated control group; bar indicates SE.
Figure 10:
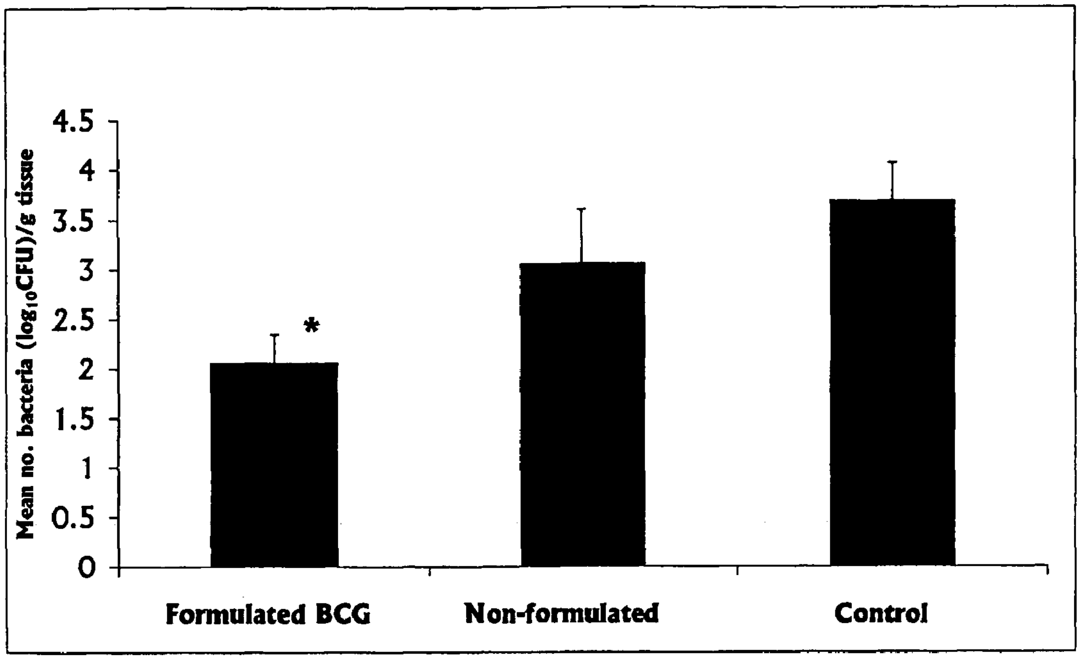
FIG. 10. Effect of oral vaccination of possums with formulated BCG on mean numbers of mycobacteria isolated from spleen following challenge with *M. bovis*. Results are expressed as the geometric mean number of CFU ($\log_{10}$)/g of tissue. *Represents a mean which is significantly different from the mean of non-vaccinated control group; bar indicates SE.

*Mycobacterium bovis* was isolated from the lung and spleens of the *M. bovis* challenged possums. The mean numbers of *M. bovis* isolated from the lungs and spleen for the different groups are shown in FIGS. 9 and 10. The mean lung bacterial counts for the non-formulated and formulated BCG groups were significantly lower than those for the non-vaccinated control group ($P<0.05$). The mean spleen bacterial counts for the formulated BCG group were approximately 10-fold less than the non-formulated BCG group and approximately 40-fold less than the non-vaccinated control group. The mean spleen bacterial counts for the formulated BCG group were significantly lower than those for non-formulated BCG and the non-vaccinated control groups ($P<0.05$).

In the second experiment which compared four oral lipid BCG formulations with subcutaneous vaccination (Table 4), spleen bacterial counts for three of the orally vaccinated groups and the subcutaneously vaccinated group were significantly lower compared to the non-vaccinated group ($P<0.05$). The remaining oral lipid BCG group (lipid N) did not show significantly reduced bacterial spleen counts. No significant differences were seen between the groups when bacterial lung counts were compared. In general, possums which did not show an immune response to vaccination (ie non-vaccinated and lipid N groups) had higher mean bacterial spleen and lung counts compared with possums that had responded to vaccination.

TABLE 1

Bovine PPD-stimulated spleen cell responses in mice 8 weeks after oral vaccination with different lipid formulations[a]

| Immunization | IL-2 (pg/ml) | IFN-γ (pg/ml) | LTA (SI) |
|---|---|---|---|
| Formulation only | 110.62 (+/−14.06) | 51.44 (+/−14.38) | 1.67 (+/−0.49) |
| Non formulated BCG | 153.51 (+/−25.22) | 65.10 (+/−20.05 | 1.83 (+/−0.51) |
| Formulation C BCG | 430.43* (+/−66.44) | 2160.95* (+/−273.40) | 16.26* (+/−1.20) |
| Formulation K BCG | 230.23 (+/−54.13) | 1268.30* (+/−76.80) | 7.26* (+/−0.83) |
| Formulation N BCG | 130.23 (+/−54.70) | 75.50 (+/−16.80) | 2.76 (+/−0.33) |

*Represents a mean which is significantly different from the mean of non-vaccinated (Formulation only) control group. P value < 0.05 (Student t test)

TABLE 2

Effect of vaccination on protection of mice against aerosol challenge with *Mycobacterium bovis*

| Vaccine Group | Lung bacterial count† | $Log_{10}$ resistance# | Spleen bacterial count | $Log_{10}$ resistance# |
|---|---|---|---|---|
| Non-vaccinated | 5.837[a] (±0.362) | NA | 4.565[a] (±0.189) | NA |
| Formulated Oral BCG | 4.774[b] (±0.270) | 1.06 | 3.084[b] (±0.176) | 1.48 |
| Subcutaneous BCG | 3.498[c] (±0.237) | 2.34 | 2.660[b] (±0.181) | 1.90 |

†Values are $log_{10}$ numbers of CFU ± standard error of *M. bovis* from the lungs and spleen of 6 animals per group 37-40 days post-challenge.
#Data are expressed as levels of $log_{10}$ resistance calculated by subtracting the $log_{10}$ mean number of bacilli in the organs of vaccinated animals from the $log_{10}$ mean number of bacilli in the organs of non-vaccinated animals,
NA-not applicable.
Figures in columns with the same superscript letter are not significantly different ($P > 0.05$).

TABLE 3

Number of possums responding to bovine PPD in the lymphocyte proliferation assay following oral vaccination.

| BCG formulation | Group size | Weeks after vaccination 0 | 4 | 6 |
|---|---|---|---|---|
| Formulated BCG | 5 | 0* | 2 | 5 |
| Non-formulated BCG | 5 | 0 | 0 | 1 |
| Control (no BCG) | 6 | 0 | 0 | 0 |

*No. of animals with stimulation index > 3.5

TABLE 4

Pathological and microbiological findings for vaccinated possums challenged with *M. bovis*

| Vaccine Group | Change in body weight/challenge weight[a] | Lung weight/PM body weight[b] | Lung bacterial count[c] | Spleen bacterial count[c] |
|---|---|---|---|---|
| Lipid C | −0.060 (±0.033) | 22.54 (±2.63) | 5.634 (±0.385) | 1.301* (±0.373) |
| Lipid K | −0.067 (±0.030) | 15.49 (±2.12) | 5.481 (±0.428) | 1.321* (±0.289) |
| Lipid N | −0.122 (±0.037) | 23.47 (±2.85) | 6.038 (±0.273) | 2.200 (±0.498) |
| Lipid F | −0.035* (±0.031) | 16.28 (±4.11) | 5.342 (±0.290) | 0.934* (±0.230) |
| sc BCG | −0.012* (±0.055) | 20.07 (±3.86) | 5.384 (±0.427) | 1.270* (±0.309) |

TABLE 4-continued

Pathological and microbiological findings for vaccinated possums challenged with *M. bovis*

| Vaccine Group | Change in body weight/challenge weight[a] | Lung weight/PM body weight[b] | Lung bacterial count[c] | Spleen bacterial count[c] |
|---|---|---|---|---|
| Non-vaccinated | −0.147 (±0.048) | 24.10 (±3.50) | 6.048 (±0.166) | 2.553 (±0.465) |

Change in body weight/challenge body weight: Lipid F, BCG < Non-vaccinated ($P < 0.05$).

Spleen bacterial count: Lipid C, Lipid K, Lipid F, BCG < Non-vaccinated; Lipid F < Lipid N ($P < 0.05$).

[a]Change in body weight between post mortem and challenge (kg)/body weight at challenge (kg)

[b]Lung weight (g)/body weight at post mortem (kg).

[c]Bacterial count, CFU $log_{10}$/g of tissue.

*Significantly different to non-vaccinated group.

INDUSTRIAL APPLICATION

The immunogenic composition includes a lipid formulation which maintains immunogens in a stable matrix, through which they are uniformly dispersed. This facilitates administration of consistent doses of immunogen, avoiding dose dumping and ineffective low dosing. The lipid formulation has also been shown by the applicants to improve storage and viability of live organisms contained therein. The lipid formulation also protects the immunogens and live organisms from degradation by stomach acids and enzymes. Losses in viability of organisms in lipid based formulations are also significantly lower than those reported for freeze-dried products. Storage under humid or moist conditions can also be achieved without deterioration because of the hydrophobic properties of the formulation.

It has been demonstrated that the viability of organisms, particularly bacteria in vaccine preparations is important for inducing strong and long lasting protective immunity. This may be achieved using the compositions of the invention. The compositions are also simple to prepare, more affordable to produce, and find increased consumer acceptance and safety where the use of needles and syringes can be avoided.

The inventive compositions may be administered in a variety of ways including subcutaneously, but are particularly amenable to oral delivery. The applicants have found that the lipid formulation in the composition can protect viability of organisms and their constituent antigens against degradation in the stomach, which enables live organisms to be taken up through the gastrointestinal mucosa for processing, replication and presentation to the immune system. Moreover, the applicants have determined that the doses to be administered can be effective at doses lower than previously anticipated for oral delivery (8).

Vaccination of wildlife, such as possums requires immunogens to be delivered by the mucosal route. Oral bait vaccines therefore represent a practical and cost effective delivery option. Oral vaccination of humans is also a more cost effective method of vaccination and likely to find favour with users.

When administered in other ways such as subcutaneously, the lipid formulation still provides protection from attack, for example, by macrophages. With subcutaneous administration, or administration by injection, the formulation of a lipid depot also allows sustained release to mimic the infection process, and facilitate the mounting of an immune response.

It will be appreciated that the compositions of the invention also provide substantial advantages over many higher cost, injectable vaccine formulations.

The compositions are effective to induce immune responses to a wide range of infectious organisms, including gastrointestinal and respiratory pathogens, and preferably tuberculosis.

The compositions of the invention may also be used as a vaccine delivery system for a wide range of immunogens, or for the co-delivery or conjugated delivery of immunogenic molecules, particularly those which for reasons of dose or antigenicity are poorly immunogenic. The compositions of the invention are also useful as vaccine adjuvants.

The invention claimed is:

1. An immunogenic composition comprising a pharmaceutically acceptable lipid formulation and at least one immunogenic component comprising an immunogenically effective amount of live organisms, the composition being formulated for oral administration, and wherein the lipid formulation is a lipid matrix in a solid or paste form and the live organisms are uniformly dispersed throughout the lipid matrix.

2. The composition according to claim 1 wherein the lipid formulation undergoes solid to fluid transition between about 10° C. to 40° C.

3. The composition according to claim 1 wherein the lipid formulation undergoes solid to fluid transition between about 30° C. to 40° C.

4. The composition according to claim 1 wherein the live organisms are a biologically pure culture.

5. The composition according to claim 1 which comprises at least two immunogenic components.

6. The composition according to claim 1 wherein the lipid formulation undergoes solid to fluid transition between about 30° C. to 37° C.

7. The composition according to claim 1 wherein the lipid formulation has the formula: 3% myristic acid; 26% palmitic acid; 15% stearic acid; 40% oleic acid; and 6% linoleic acid.

8. The composition according to claim 1 which is essentially free of aqueous components.

9. The composition according to claim 1 wherein the composition consists essentially of said live organisms and lipid.

10. A method for simulating a mucosal immune response in an animal, the method comprising administering to said animal a composition according to claim 1.

11. A composition according to claim 1 which further comprises one or more flavoring agents, attractants or odorants.

12. The composition according to claim 1 wherein the lipid formulation comprises 47% lauric acid, 20% myristic acid, 12% palmitic acid, 12% stearic acid, and 3% oleic acid.

13. The composition according to claim 1 wherein the lipid matrix is a coconut oil.

14. The composition of claim 1, wherein said composition is protectively coated.

15. The composition of claim 14, wherein the protective coating is gelatin.

16. A method for immunizing an animal, the method comprising administering to said animal a composition according to claim 1.

17. The method according to claim 16 wherein the animal is human.

18. The method according to claim 16 wherein the animal is a cattle, deer, sheep, possum or badger.

19. The composition according to claim 1 wherein the live organisms are selected from the group consisting of fungi, protozoa, bacteria, and viruses.

20. The composition according to claim 19 wherein the virus is HIV or SIV.

21. The composition according to claim 19 wherein the bacteria is selected from *Brucella,* Anthrax, and *Mycobacterium.*

22. The composition according to claim 21 wherein the bacteria is *Mycobacterium.*

23. The composition according to claim 22 wherein the *Mycobacterium* is selected from *M. tuberculosis* complex (comprising *M. tuberculosis, M. bovis, M. africanum* and *M. microtii*) *M. avium-intracellulare* complex (comprising *M. intracellulare* and *M. avium*), *M. paratuberculosis, M. vaccae, M. smegmatis, M. chelonae, M. fortiutum, M. kansasii, M. leprae, M. marinum, M. ulcerans, M. simiae, M. haemophilum, M. malmoense, M. shimoidei, M. gastri, M. terrae* complex, and *M. monchromogenicum*, including functionally equivalent variants, natural or genetically engineered clones, mutants, and recombinants of these strains, and immunogenic components thereof.

24. The composition according to claim 22 wherein the *Mycobacterium* is *M. bovis.*

25. The composition according to claim 24 wherein the *M. bovis* is Bacille Calmette Guerin (BCG).

26. The composition according to claim 24 wherein the *M. bovis* is BCG Danish strain 1331.

27. The composition according to claim 24 wherein the *M. bovis* is the BCG Brazilian strain.

28. The composition according to claim 24 wherein the *M. bovis* is the BCG Pasteur 1173P2 strain.

29. The composition according to claim 22 wherein the *Mycobacterium* is present in a concentration of $1\times10^5$ to $1\times10^{10}$ colony forming units (CFU)/ml.

30. The composition according to claim 22 wherein the *Mycobacterium* is present in a concentration of $1\times10^7$ to $1\times10^9$ colony forming units (CFU)/ml.

31. An immunogenic composition comprising a pharmaceutically acceptable lipid formulation which undergoes solid to fluid transition between about 10° C. to 40° C., and at least one immunogenic component present in an immunogenically effective amount, wherein the lipid formulation is a lipid matrix in a solid form or paste form and the immunogenic component is uniformly dispersed throughout the lipid matrix.

32. The composition according to claim 31 wherein the lipid formulation undergoes solid to fluid transition between about 30° C. to 40° C.

33. The composition according to claim 31 which is formulated for parenteral administration.

34. The composition according to claim 31 which is formulated for subcutaneous administration.

35. The composition according to claim 31 which is formulated for oral administration.

36. The composition according to claim 31 wherein the composition consists essentially of lipid and said at least one immunogenic component.

37. The composition according to claim 31 which comprises at least two immunogenic components.

38. The composition according to claim 31 wherein the lipid formulation undergoes solid to fluid transition between about 30° C. to 37° C.

39. The composition according to claim 31 wherein the lipid formulation has the formula: 3% myristic acid; 26% palmitic acid; 15% stearic acid; 40% oleic acid; and 6% lineolic acid.

40. A method for stimulating a mucosal immune response in an animal, the method comprising administering to said animal a composition according to claim 31.

41. The composition of claim 31, wherein said composition is protectively coated.

42. The composition of claim 31 wherein the lipid matrix is a coconut oil.

43. The composition according to claim 31 wherein the lipid formulation comprises 47% lauric acid, 20% myristic acid, 12% palmitic acid, 12% stearic acid, and 3% oleic acid.

44. The composition according to claim 31 wherein the immunogenic component comprises live organisms, a protein, glycoprotein, peptide, or mixtures thereof.

45. The composition according to claim 44 wherein the immunogenic component is isolated and/or purified.

46. The composition according to claim 44 wherein the live organisms are a biologically pure culture.

47. The composition according to claim 31 which is essentially free of aqueous components.

48. A composition according to claim 31 which further comprises one or more flavoring agents, attractants or odorants.

49. A method for immunizing an animal, the method comprising administering to said animal a composition according to claim 31.

50. The method according to claim 49 wherein the administration is parenteral administration.

51. The method according to claim 49 wherein the administration is oral administration.

52. The method according to claim 49 wherein the administration is subcutaneous administration.

53. The method according to claim 49 wherein the animal is human.

54. The method according to claim 49 wherein the animal is a cattle, deer, sheep, possum or badger.

* * * * *

UNITED STATES PATENT AND TRADEMARK OFFICE

CERTIFICATE OF CORRECTION

PATENT NO. : 7,758,869 B2
APPLICATION NO. : 10/484688
DATED : July 20, 2010
INVENTOR(S) : Frank Ernest Aldwell et al.

It is certified that error appears in the above-identified patent and that said Letters Patent is hereby corrected as shown below:

Title page, item [73], delete the Assignee "Immune Solutions Limited, Dunedin (NZ)" and add Assignees --Otago Innovation Limited, (NZ), Animal Health Board, Inc., Wellington (NZ), Agresearch Limited, Hamilton (NZ)--.

Signed and Sealed this
Twenty-fifth Day of October, 2011

David J. Kappos
*Director of the United States Patent and Trademark Office*